(12) United States Patent
Hoffmann et al.

(10) Patent No.: US 7,378,406 B2
(45) Date of Patent: May 27, 2008

(54) USE OF ANTIPROGESTINS FOR PROPHYLAXIS AND TREATMENT OF HORMONE-DEPENDENT DISEASES

(75) Inventors: Jens Hoffmann, Muehlenbeck (DE); Rosemarie Lichtner, Berlin (DE); Gerhard Siemeister, Berlin (DE); Martin Schneider, Berlin (DE); Ulrike Fuhrmann, Berlin (DE)

(73) Assignee: Schering AG, Berlin (DE)

( * ) Notice: Subject to any disclaimer, the term of this patent is extended or adjusted under 35 U.S.C. 154(b) by 644 days.

(21) Appl. No.: 10/399,320

(22) PCT Filed: Oct. 17, 2001

(86) PCT No.: PCT/EP01/12005

§ 371 (c)(1), (2), (4) Date: Sep. 8, 2003

(87) PCT Pub. No.: WO02/32430

PCT Pub. Date: Apr. 25, 2002

(65) Prior Publication Data

US 2004/0048841 A1  Mar. 11, 2004

Related U.S. Application Data

(60) Provisional application No. 60/240,998, filed on Oct. 18, 2000.

(30) Foreign Application Priority Data

Oct. 18, 2000 (EP) .................. 002503415

(51) Int. Cl.
A61K 31/56 (2006.01)

(52) U.S. Cl. .................... 514/182

(58) Field of Classification Search ........... 514/182
See application file for complete search history.

(56) References Cited

U.S. PATENT DOCUMENTS

| | | | |
|---|---|---|---|
| 6,316,432 B1 | 11/2001 | Schwede et al. | |
| 6,503,895 B2 | 1/2003 | Schwede et al. | |
| 6,806,263 B2 | 10/2004 | Schwede et al. | |
| 7,148,213 B2 | 12/2006 | Schwede et al. | |

FOREIGN PATENT DOCUMENTS

| | | | |
|---|---|---|---|
| CA | 2280041 | * | 8/1998 |
| DE | 19706061 | | 8/1998 |

OTHER PUBLICATIONS

Fuhrmann Ulrike et al., "Synthesis and Biological Activity of a Novel, Highly Potent Progesterone Receptor Antagonist," Journal of Medical Chemistry, Dec. 7, 2000, pp. 5010-5016, vol. 43, No. 26, XP001064233, ISSN: 0022-2623, the whole document, American Chemical Society, Washington, DC.

* cited by examiner

Primary Examiner—San-Ming Hui
(74) Attorney, Agent, or Firm—Millen, White, Zelano & Branigan, P.C.

(57) ABSTRACT

The present invention relates to methods and uses for preventing or treating hormone-dependent disease, in particular breast cancer, in a mammal by antiprogestins, in particular antiprogestin 11β-(4-acetylphenyl)-17β-hydroxy-17α-(1,1,2,2,2-pentafluoroethyl)-estra-4,9-dien-3-one or a pharmaceutically acceptable derivative or analogue thereof. The invention further relates to pharmaceutical compositions comprising said antiprogestin.

15 Claims, 6 Drawing Sheets

USE OF ANTIPROGESTINS FOR PROPHYLAXIS AND TREATMENT OF HORMONE-DEPENDENT DISEASES

This application claims benefit of U.S. Provisional application No. 60/240,998, filed Oct. 18, 2000 and European application No. 00250341.5, filed Oct. 18, 2000, and is a 371 of PCT/EP01/12005 of Oct. 18, 2001.

FIELD OF THE INVENTION

The present invention relates to the use of antiprogestins for the prophylaxis and treatment of hormone-dependent diseases, in particular breast cancer. The present invention further relates to pharmaceutical compositions and dosage forms comprising antiprogestins for the prophylaxis and treatment of hormone-dependent diseases, in particular breast cancer. A particularly preferred antiprogestin for use in the invention is the antiprogestin 11β-(4-acetylphenyl)-17β-hydroxy-17α-(1,1,2,2,2-pentafluoroethyl)-estra-4,9-dien-3-one or a pharmaceutically acceptable derivative or analogue thereof.

BACKGROUND OF THE INVENTION

Endocrine therapy represents a mainstay of effective, minimally toxic, palliative treatment for metastatic breast cancer. As a standard palliative treatment of non-operable mammary carcinomas as well as for adjuvant therapy after primary treatment of mammary carcinomas predominantly the antiestrogen tamoxifen is used. However, tamoxifen cannot cure breast cancer. Thus, for secondary therapy progestins or aromatase inhibitors are commonly used. In premenopausal women ovariectomy, tamoxifen and LHRH (luteinizing hormone releasing hormone) analogs achieve comparable results (H. T. Mouridson et al., *Eur. J. Cancer Clin. Oncol.*, 24, pp. 99-105, 1988).

Although tamoxifen is widely used for adjuvant therapy of breast cancer, its use as a chemopreventive agent is problematic, because it has been shown that the treatment results in an increase in the incidence of endometrial cancers (I. N. White, *Carcinogenesis*, 20(7): 1153-60, 1999).

Antiprogestins represent a relatively new and promising class of therapeutic agents that could have significant impact on breast cancer treatment. Although antiprogestins were originally created with regard to medicinal non-surgical termination of pregnancy (EP 129 499), certain antiprogestins have recently gained importance in the endocrine therapy of those breast cancers involving receptors for progesterone (T. Maudelonde et al., in: J. G. M. Klijn et al., *Hormonal Manipulation of Cancer: Peptides, Growth Factors and New (Anti) Steroidal Agents*, Raven Press, New York, 1987, pp. 55-59). This new strategy in endocrine therapy is based on the antitumor activity of antiprogestins in progesterone receptor-positive human breast cancer cell lines in vitro and in several hormone-dependent mammary tumors of the mouse and rat in vivo. In particular, the antitumor mechanism of the antiprogestins onapristone and mifepristone (RU 486) was investigated using the hormone-dependent MXT mammary tumor model of the mouse as well as the DMBA- and the NMU-induced mammary tumor models of the rat (M. R. Schneider et al., *Eur. J. Cancer Clin. Oncol.*, Vol. 25, No. 4, pp. 691-701, 1989; H. Michna et al., *Breast Cancer Research and Treatment* 14:275-288, 1989; H. Michna, *J. Steroid. Biochem.* Vol. 34, Nos 1-6, pp. 447-453, 1989). However, due to low activity and adverse side effects involved with e.g. mifepristone this compound could not be recommended as a single agent in the management of breast cancer (D. Perrault et al., *J Clini. Oncol.* 1996 October 14(10), pp. 2709-2712).

Antiprogestin compounds are suitable for initiating abortions and thus for use in postcoital fertility control, as contraceptives for women (WO-A 93/23020, WO-A 93/21927) and further for the treatment of hormone irregularities, for initiating menstruation and for initiating labor. Further indications are in the field of hormone substitution therapy (WO-A 94/18983), the treatment of afflictions related to dysmenorrhea and the treatment of endometriosis (EP-A 0 266 303) as well as myomas.

17 α-fluoroalkylsteroids having strong antiprogestin activity as well as methods for producing them are described in WO 98/34947.

Antiprogestins of the prior art tested or used previously due to their antitumor activity frequently exhibited certain disadvantages.

For example, despite the fact that prior art antiprogestins exhibited antigestagenic activity, these compounds were not suitable treatments for hormone-dependent diseases such as breast cancer. In particular, prior art compounds were associated with side effects, e.g. mifepristone exhibits strong antiglucocorticoid side effects (cf. L. M. Kettel et al., *Fertil. Steril.* 1991 September, 56(3), pp. 402-407; X. Bertagna, *Psychoneuroendocrinology* 1997; 22 Suppl. 1, pp. 51-55) and besides it showed only moderate activity in clinical trials (see again D. Perrault et al., *J. Clin. Oncol.* 1996 October, 14(10), pp. 2709-2712). Regarding side effects of other hormone-based therapies, as already mentioned above, tamoxifen administration can result in an increase in the incidence of endometrial cancers (I. N. White, *Carcinogenesis*, 20(7):1153-60, 1999).

Another problem with prior art antiprogestins was poor bioavailability when administered orally. Thus, they generally had to be administered in high doses, giving rise to possible unfavorable side effects. Moreover, oral administration is desirable with respect to patient convenience and compliance.

Furthermore, there is still a need for compounds that are active not only in the treatment, but also in the prophylaxis of breast cancer and other hormone-dependent diseases. The increased incidence of endometrial cancer associated with tamoxifen tends to show that this compound is unsuitable for prophylaxis treatment of healthy women, and no other suitable compounds are available (cf. L. Bergman et al., *The Lancet*, Vol. 356, Sep. 9, 2000; 881-887).

OBJECT OF THE PRESENT INVENTION

It is an object of the present invention to prevent or reduce the disadvantages of the prior art methods for preventing or treating hormone-dependent diseases, such as breast cancer. It is especially desired that a means of preventing and treating hormone-dependent diseases, such as breast cancer, via the administration of highly effective agents is provided that is superior to known methods and agents, including ovariectomy. Thus it is further especially desired to provide a treatment of hormone-dependent diseases, such as breast cancer, that prevents serious and risk-laden surgery involved with ovariectomy. It is further desired to provide an agent for use according to the invention exhibiting less side effects than previously known or suggested methods for treating and preventing hormone-dependent diseases such as breast cancer.

It is a further object of the present invention to provide pharmaceutical compositions comprising highly effective antitumor agents for the prophylaxis and treatment of breast cancer and other hormone-dependent diseases.

These objects are surprisingly achieved by the use of antiprogestins according to the present invention and by pharmaceutical compositions and dosage forms comprising such antiprogestins. Particularly preferred in this regard is the antiprogestin 11β-(4-acetylphenyl)-17β-hydroxy-17α-(1,1,2,2,2-pentafluoroethyl)-estra-4,9-dien-3-one or a pharmaceutically acceptable derivative or analogue thereof.

It is a further object of the present invention to provide antiprogestins, such as the antiprogestin 11β-(4-acetylphenyl)-17β-hydroxy-17α-(1,1,2,2,2-pentafluoroethyl)-estra-4,9-dien-3-one or pharmaceutically acceptable derivatives or analogues thereof, that are particularly suitable for oral administration.

SUMMARY OF THE INVENTION

The present invention is based on the novel and unexpected observation that certain antiprogestins, in particular 11β-(4-acetylphenyl)-170-hydroxy-17α-(1,1,2,2,2-pentafluoroethyl)-estra-4,9-dien-3-one or a pharmaceutically acceptable derivative or analogue thereof, are exceptionally active in the prevention and reduction of tumor growth in DMBA (7,12-dimethylbenzanthracene)- and NMU (N-methylnitrosourea)-induced breast cancer models. In fact, the antiprogestin 11β-(4-acetylphenyl)-17β-hydroxy-17α-(1,1,2,2,2-pentafluoroethyl)-estra-4,9-dien-3-one (I) turned out to be distinctly more potent than tamoxifen and ovariectomy in the prevention of breast cancer development.

Thus, the present invention provides a method for prophylaxis and treatment of breast cancer and other hormnone-dependent diseases in mammals, in particular humans, in need of such treatment, said method comprising administering a pharmaceutically effective amount of an antiprogestin, in particular 11β-(4-acetylphenyl)-17β-hydroxy-17α-(1,1,2,2,2-pentafluoroethyl)-estra-4,9-dien-3-one, or a pharmaceutically acceptable derivative thereof or analogue thereof, to a patient.

The present invention further provides pharmaceutical compositions comprising an antiprogestin, in particular 11β-(4-acetylphenyl)-17β-hydroxy-17α-(1,1,2,2,2-pentafluoroethyl)-estra-4,9-dien-3-one or a pharmaceutically acceptable derivative or analogue thereof, in an amount sufficient for the prophylaxis or treatment of breast cancer or other hormone-dependent diseases.

The preferred antiprogestin 11β-(4-acetylphenyl)-17β-hydroxy-17α-(1,1,2,2,2-pentafluoroethyl)-estra-4,9-dien-3-one will hereinafter be referred to as "antiprogestin (I)".

DETAILED DESCRIPTION OF THE INVENTION

Antiprogestin (I)—11β-(4-acetylphenyl)-17β-hydroxy-17α-(1,2,2,2-pentafluoroethyl)-estra-4,9-dien-3-one—is represented below by formula (I):

Antiprogestin (I) (or a pharmaceutically acceptable derivative or analogue thereof having comparable activity) is a valuable pharmaceutical agent having strong antiprogestin activity. Antiprogestin (I), as well as further antiprogestins, can be used according to the present invention for the prophylaxis and treatment of breast cancer and other hormone-dependent diseases.

The term "antiprogestin" in the context of the present invention is intended to primarily comprise all compounds being capable of competitively inhibiting progesterone receptors. However, it should also encompass compounds capable of inhibiting the biosynthesis of progestins.

A pharmaceutically acceptable derivative or analogue of antiprogestin (I) in the context of the present invention may include, for example, any one of the inventive compounds disclosed in WO 98/34947.

The term "hormone-dependent diseases" in the context of the present invention may include, but is not limited to, breast cancer, ovarian cancer, endometrial cancer, myeloma, anovulatory infertility, meningoma, i.e. diseases which substantially originate or are influenced by the presence of hormone receptors and/or hormone-dependent pathways.

As regards the superiority of the present invention over the prior art, it is especially favorable that, e.g., in antiprogestin (I) used according to the present invention further endocrine side effects, such as e.g. androgen, estrogen or antiglucocorticoid activity are only very weak, if present at all. Due to the high bioavailability of antiprogestin (I) it can be administered orally, thus rendering the treatment for a patient in need thereof as convenient as possible. As a further favorable consequence, antiprogestin (I) is well tolerated and can be administered in relatively low doses compared to established treatments thus reducing undesirable side effects, such as an increase in the incidence of endometrial cancers with the administration of tamoxifen (see I. N. White, *Carcinogenesis*, 20(7):1153-60, 1999; L. Bergman et al., The Lancet, Vol. 356, Sep. 9, 2000, 881-887) as well as the antiglucocorticoid effects and certain toxic side effects related to the administration of mifepristone (see D. Perrault et al., *J. Clin. Oncol.* 1996 October 14(10), pp. 2709-2712; L. M. Kettel et al., *Fertil. Steril.* 1991 September, 56(3), pp. 402-407; X. Bertagna, *Psychoneuroendocrinology* 1997, 22 Suppl. 1; pp. 51-55).

A further advantage of the present invention over the prior art is the provision of an effective method for the prophylaxis of hormnone-dependent diseases such as breast cancer, such that patients under high risk of developing or redeveloping hormone-dependent diseases can be treated in advance to avoid incidence of such diseases.

In a first aspect the present invention relates to a method for the prophylaxis or treatment of breast cancer and other hormone-dependent diseases, comprising administering at least one antiprogestin, preferably antiprogestin (I) or a pharmaceutically acceptable derivative or analogue thereof to a mammal, preferably a human, in need of such prophylaxis or treatment.

In a further aspect the present invention relates to the use of antiprogestins as defined above, preferably antiprogestin (I) or a pharmaceutically acceptable derivative or analogue thereof, for the manufacture of a medicament, in particular for the prophylaxis or treatment of breast cancer or other hormone-dependent diseases.

In another aspect the present invention relates to pharmaceutical compositions comprising at least one antiprogestin as defined above, preferably antiprogestin (I) or a pharmaceutically acceptable derivative or analogue thereof. Optionally the antiprogestin (I) can be combined with other pharmacologically active agents. For example, the antiprogestin may also be combined with a cytotoxic agent for treatment by coupling to a hormone receptor.

The manufacture of the medicaments may be performed according to methods known in the art. Commonly known and used adjuvants as well as further suitable carriers or diluents may be used. Suitable carriers and adjuvants may be such as recommended for pharmacy, cosmetics and related fields in: *Ullmann's Encyclopedia of Technical Chemistry*, Vol. 4, (1953), pp. 1-39; *Journal of Pharmaceutical Sciences*, Vol. 52 (1963), p. 918ff; H. v. Czetsch-Lindenwald, "Hilfsstoffe für Pharmazie und angrenzende Gebiete"; *Pharm. Ind.* 2, 1961, p. 72ff, Dr. H. P. Fiedler, *Lexikon der Hiffsstoffe für Pharmazie, Kosmetik und antgreizzeiide Gebiete*, Cantor K G, Aulendorf in Württemberg, 1971.

Antiprogestins suitable for the purposes of the present invention, preferably antiprogestin (I) or a pharmaceutically acceptable derivative or analogue thereof, can be incorporated into pharmaceutical compositions according to known methods of preparing galenics for oral or parenteral, e.g., intraperitoneal, intramuscular, subcutaneous or percutaneous application. They can also be implanted into tissue. Implants can comprise as inert materials e.g. biologically degradable polymers or synthetic silicones such as e.g. silicone rubber.

They can be administered in the form of tablets, pills, dragees, gel capsules, granules, suppositories, implants, injectable sterile aqueous or oily solutions, suspensions or emulsions, ointments, creams, gels or by intravaginal (e.g., vaginal rings) or intrauterine systems (e.g., diaphragms, loops).

For the preparation of pharmaceutical compositions for oral administration, the antiprogestins suitable for the purposes of the present invention as defined above can be admixed with commonly known and used adjuvants and carriers such as for example, gum arabic, talcum, starch, sugars such as, e.g., mannitose, methyl cellulose, lactose, gelatin, surface-active agents, magnesium stearate, aqueous or non-aqueous excipients, paraffin derivatives, cross-linking agents, dispersants, emulsifiers, lubricants, conserving agents and flavoring agents (e.g., ethereal oils). In the pharmaceutical composition, the antiprogestin may be dispersed in a microparticle, e.g. a nanoparticulate, composition.

In order to further enhance the bioavailability of the active agent, the antiprogestins suitable for the purposes of the present invention as defined above can also be formulated as cyclodextrin clathrates by reacting them with α-, β- or γ-cyclodextrines or derivatives thereof according to the method as disclosed in PCT/EP95/02656.

For parenteral administration the antiprogestins suitable for the purposes of the present invention as defined above can be dissolved or suspended in a physiologically acceptable diluent, such as, e.g., oils with or without solubilizers, surface-active agents, dispersants or emulsifiers. As oils for example and without limitation, olive oil, peanut oil, cottonseed oil, soybean oil, castor oil and sesame oil may be used.

The amount to be administered (i.e., a "pharmaceutically effective amount") varies within a broad range and depends on the condition to be treated and the mode of administration. It can cover any amount efficient for the intended treatment. Determining a "pharmaceutically effective amount" is within the purview of the person skilled in the art.

One unit dose may represent about 0.1 to 100 mg active agent(s). For administration to humans, the daily dose of the active agent(s) is about 0.1 to 400 mg, preferably 10 to 100 mg, most preferably 50 mg.

The pharmaceutical compositions according to the present invention can also be administered via a depot injection, an implant preparation or an IUD (internal uterine device), optionally for sustained delivery of the active agent(s).

The preferred mode of administration is oral administration. The antiprogestins for use according to the invention, and in particular, antiprogestin (I) or a pharmaceutically acceptable derivative or analogue thereof are particularly suitable for oral administration.

According to all aspects of the present invention it is also possible to combine at least one antiprogestin as defined above, in particular antiprogestin (I) or a pharmaceutically acceptable derivative or analogue thereof, with at least one antiestrogen, because many hormone-dependent diseases, in particular breast cancer, exhibit not only progesterone receptors, but also estrogen receptors. The antiestrogen may be administered either simultaneously with or sequentially to the antiprogestin, and in particular with/to antiprogestin (I) or a pharmaceutically acceptable derivative or analogue thereof. The amount of antiprogestin and antiestrogen may be equal or one component may be more predominant than the other, such as in an antiprogestin:antiestrogen ratio of 1:50 to 50:1, preferably 1:30 to 30:1, and most preferably 1:15 to 15:1.

Examples of suitable antiestrogens for use according to the invention are non-steroidal antiestrogens, such as tamoxifen and nafoxidine as well as raloxifen and EM800 and the steroidal antiestrogen faslodex. Examples of steroidal antiestrogens include those disclosed in EP 0 348 341 A and those disclosed in WO 98/07740, in particular, 11β-flouro-7α-{5-[N-methyl-N-3-(4,4,5,5,5-pentaflouropentylthio-propylamino]-pentyl}-estra-1,3,5(10)-trien-3,17β-diol, or those disclosed in WO 99/33855, in particular 11β-flouro-7α-{5-[methyl-(7,7,8,8,9,9,10,10,10-nonafluoro-decyl)-amino]-pentyl}-estra-1,3,5(10)-trien-3,17β-diol or pharmaceutically acceptable derivatives or analogues thereof. Aromatase inhibitors having an antiestrogenic effect, such as those disclosed on pages 7 to 8 of EP 0 495 825 B1 may also be used as antiestrogens.

The invention is further illustrated in the examples. The following examples are not to be understood as a limitation.

EXAMPLES

Example 1

DMBA-Induced Breast Cancer Model in Rat (Prevention Experiment)

Materials and Methods

Immature female Sprague-Dawley rats (49-51 days old; 10 animals/group) were used in this study. The carcinogen 7,12-dimethylbenz[a]anthracene (DMBA) was given as a single oral administration (10 mg). Treatment was started 20 days later as followed: 1) solvent control, 2) ovariectomy at treatment start, 3) tamoxifen, 1 mg/kg s.c., 4) antiprogestin (I), 3 mg/kg, s.c., 6 days/week. Rats were examined weekly for breast tumors by palpation. As a parameter for the prophylactic effect the tumor incidence (number of animals/group with tumors in %) was determined. For a further description and evaluation of DMBA and NMU prevention models, see R. G. Metha, *European Journal of Cancer* 36 (2000), pp. 1275-1282.

Results

In the control group all rats developed mammary tumors within 10 weeks after treatment start (incidence 100%) and progressive tumor growth was observed. Prophylactic treatment with the antiprogestin (I) prevented the tumor development for 12 weeks completely, and at the end of the experiment, after 22 weeks, in only one rat a tumor was detected (incidence 10%). After ovariectomy at the end of the experiment 40% of the rats had developed tumors. In comparison, treatment with the antiestrogen tamoxifen reduced the tumor incidence only to 60% (see FIG. 1)

Conclusion

Figure 1:
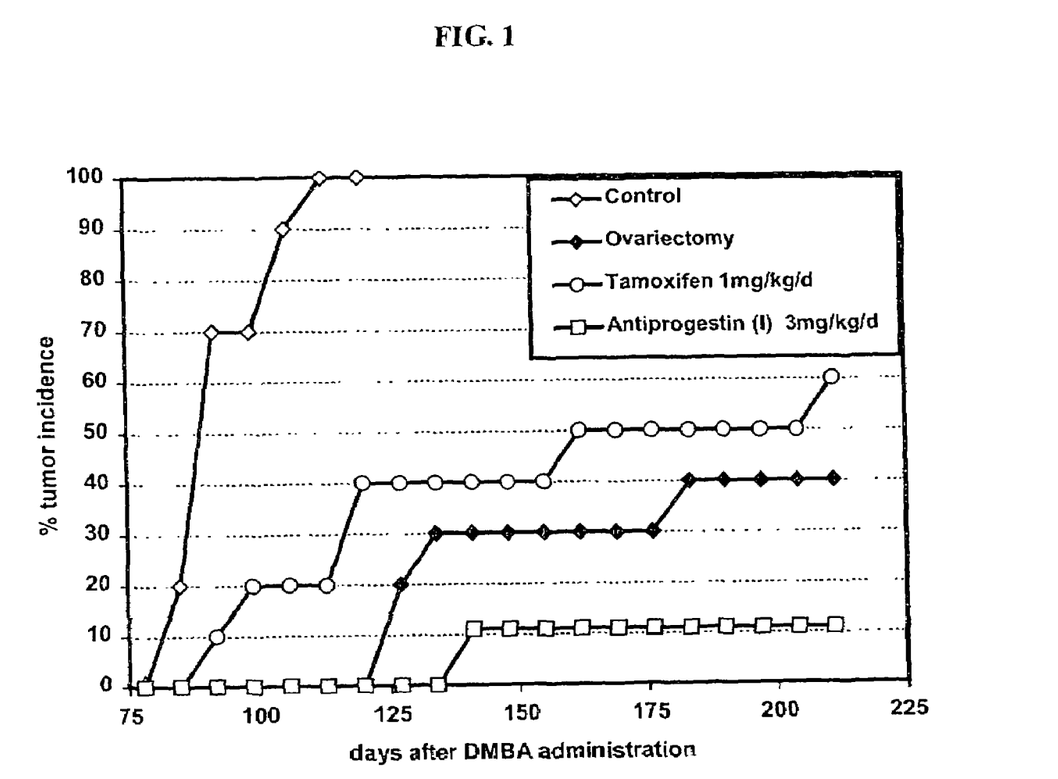
FIG. 1 shows the tumor development prevention effect of antiprogestin (I) in the DMBA-induced mammary carcinoma of the rat, compared with a control, tamoxifen and ovariectomy.

In the DMBA-induced mammary tumor model in the rat, the antiprogestin (I) completely suppressed the tumor development in intact animals for more than 12 weeks after treatment start. FIG. 1 clearly shows the superiority in activity of antiprogestin (I) over the conventional anti-breast cancer reagent tamoxifen and even over standard estrogen deprivation therapy (ovariectomy) with respect to prophylactic treatment. Antiprogestin (I) is thus superior to the established standard therapy for preventing breast cancer in women under high risk of developing the disease (tamoxifen prophylactic therapy).

These and the following results indicate that the use of antiprogestin (I) for the prophylaxis and treatment of breast cancer is superior to established standard treatments.

Example 2

DMBA-Induced Breast Cancer Model in Rat (Therapy Experiment/Dose-Response Study)

Materials and Methods

Immature female Sprague-Dawley rats (49-51 days old; 10 animals/group) were used in this study. Mammary tumors were induced by a single oral administration of 10 mg 7,12-dimethylbenz[a]anthracene (DMBA, Serva/Heidelberg). Rats with at least one established tumor with a size of more than 150 mm² were treated for 4 weeks by: 1) solvent control, 2) ovariectomy at treatment start, 3) antiprogestin (I), 0.5 mg/kg s.c., 4) antiprogestin (I), 2 mg/kg s.c., 5) antiprogestin (I), 5 mg/kg s.c., 6) antiprogestin (I), 10 mg/kg s.c., and 7) onapristone, 5 mg/kg, s.c., daily. As a parameter for growth inhibition the change of tumor area (in % with respect to initial tumor size) determined by weekly caliper measurements was used. For statistical analysis of intergroup differences of mean values the Kruskal-Wallis-test was used.

Results

Figure 2:
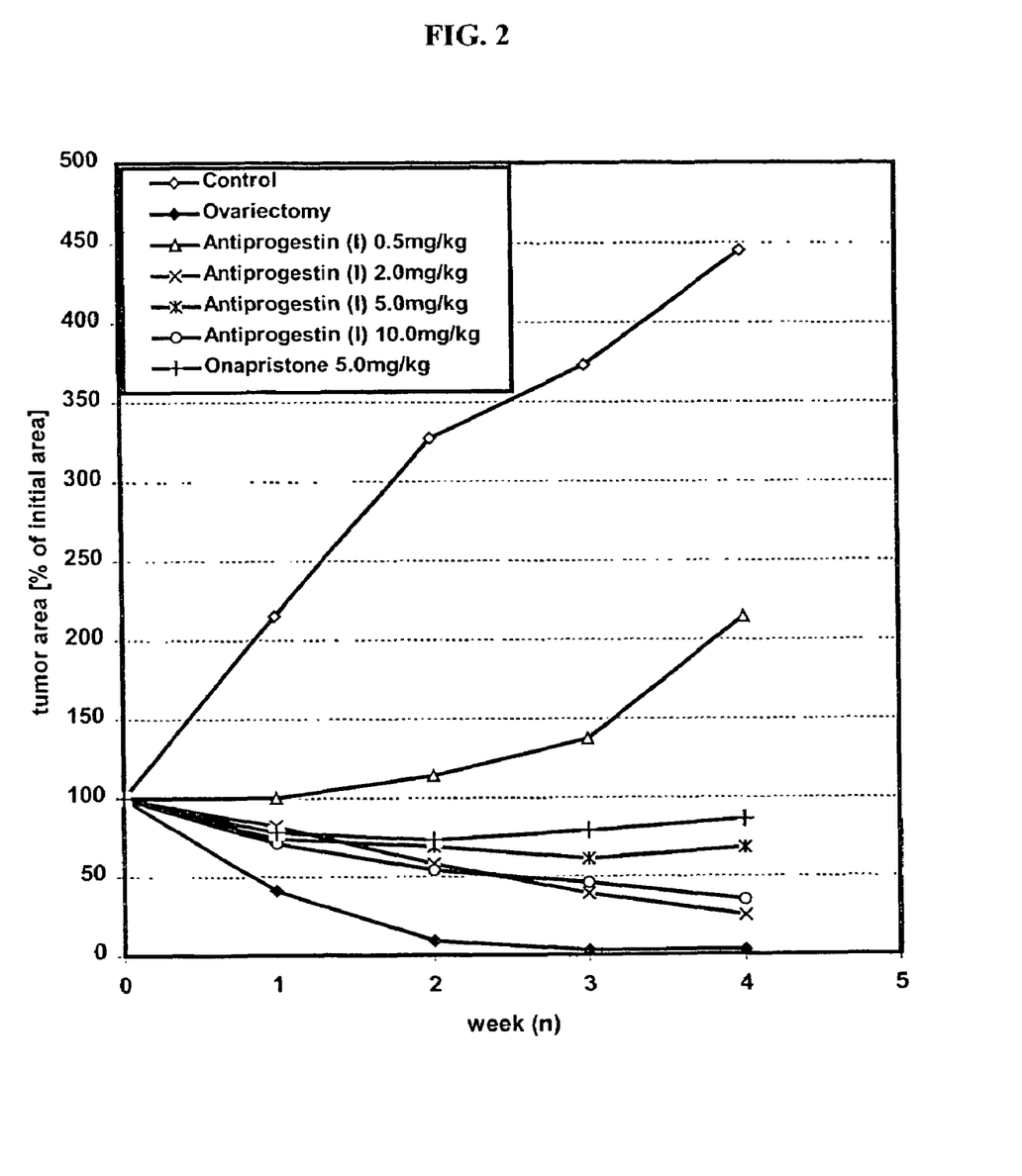
FIG. 2 shows the tumor growth inhibiting effects of antiprogestin (I) in a dose-response study in the DMBA-induced mammary carcinoma of the rat, compared with a control, the antiprogestin onapristone as well as ovariectomy. The study was performed with 0.5, 2.0, 5.0 and 10.0 mg/kg s.c. doses of antiprogestin (I).

In intact control animals, progressive tumor growth was observed, whereas ovariectomy caused a considerable tumor regression in 90% of the animals. Treatment with antiprogestin (I) at doses of or above 2 mg/kg resulted in a significant inhibition of tumor growth compared with the control (see FIG. 2). There was a clear dose-response relationship. Whereas treatment with 0.5 mg/kg antiprogestin (I) did not significantly prevent the tumor from growing, at 2 mg/kg maximal growth inhibition was observed. In this group a complete tumor regression was seen in 50% of the rats. The effect of the highest dose of antiprogestin (I) tested in this experiment (10 mg/kg), was comparable to that of 2 mg/kg. Onapristone (5 mg/kg, s.c.) was distinctly less effective than antiprogestin (I) at comparable doses.

Conclusion

In the DMBA-induced mammary tumor model in the rat, antiprogestin (I) completely suppresses the tumor growth in intact animals. It was found that 2 mg/kg antiprogestin (I) has a maximal effect on tumor growth. Antiprogestin (I) was distinctly superior to onapristone.

Example 3

NMU-Induced Breast Cancer Model in Rat (Prevention Experiment)

Materials and Methods

Tumors were induced by a single intravenous injection of NMU (nitrosomethylurea, 50 mg/kg) in female Sprague-Dawley rats (obtained from Tierzucht Schonwalde, age 50-55 days). Treatment was started 10 days later as followed: 1) solvent control, 2) ovariectomy at treatment start, 3) tamoxifen, 3 mg/kg s.c., 4) antiprogestin (I), 3 mg/kg, s.c., 5) letrozole, 3 mg/kg s.c., 6) raloxifen, 3 mg/kg s.c., 6 days/week. Rats were examined weekly for breast tumors by palpation. As a parameter for the prophylactic effect the tumor incidence (number of animals/group with tumors in %) was determined. For a further description and evaluation of DMBA and NMU prevention models, see R. G. Metha, *European Journal of Cancer* 36 (2000), pp. 1275-1282.

Results

Figure 3:
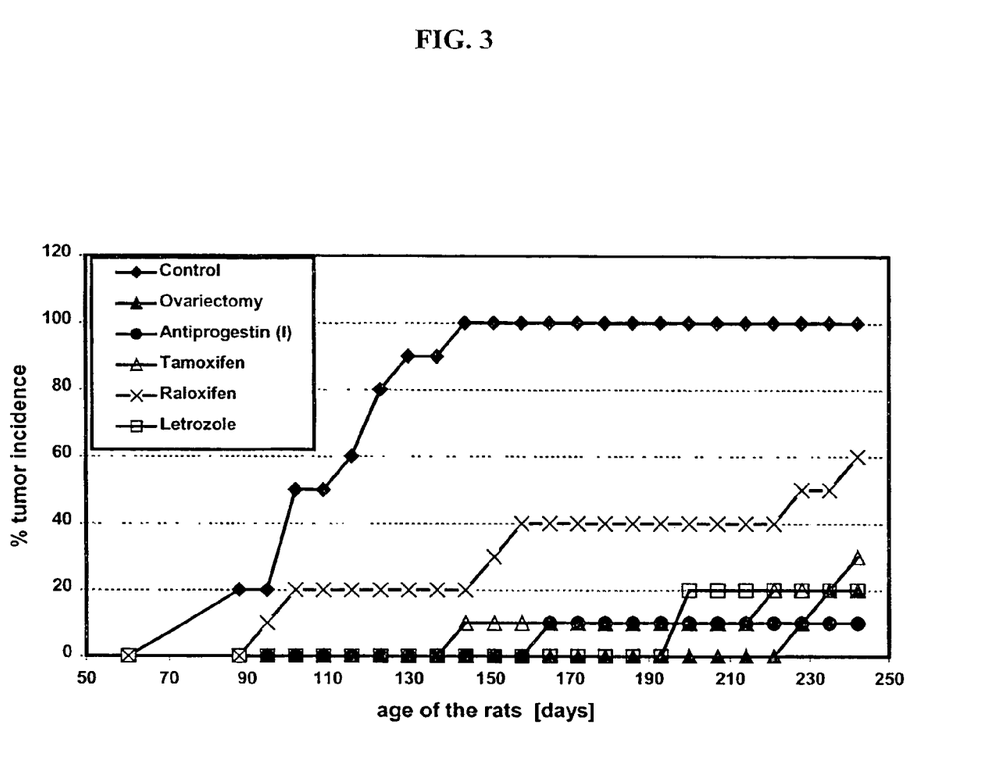
FIG. 3 shows the tumor development prevention effect of antiprogestin (I) in the NMU-induced mammary carcinoma of the rat, compared with a control, the antiestrogens raloxifen and tamoxifen, the aromatase inhibitor letrozol as well as ovariectomy.

In the control group all rats developed mammary tumors within 10 weeks after treatment start (incidence 100%; see FIG. 3) and progressive tumor growth was observed. Prophylactic treatment with the antiprogestin (I) prevented the tumor development for 12 weeks completely, and at the end of the experiment, after 27 weeks, in only one rat a tumor was detected (incidence 10%). In comparison, in treatment with the other antiestrogens or the aromatase inhibitor letrozole the tumor incidence was reduced only to 20-60%. After ovariectomy at the end of the experiment 20% of the rats had developed tumors.

Conclusion

In the NMU-induced mammary tumor model in the rat, antiprogestin (I) completely suppressed the tumor development in intact animals for more than 12 weeks after treatment start. The effect of the prophylactic treatment by antiprogestin (I) was superior to that of conventional anti-estrogens for breast cancer therapy (i.e., raloxifen, tamoxifen) and aromatase inhibitor letrozol and to standard estrogen deprivation therapy (ovariectomy) regarding tumor incidence and tumor growth.

As in the DMBA-induced tumor model (see Example 1), these results indicate that antiprogestin (I) effectively prevents the development of breast tumors in a manner which is superior to the standard prophylactic treatment, e.g. with tamoxifen.

Example 4

NMU-Induced Breast Cancer Model in Rat (Therapy Experiment)

Materials and Methods

Tumors were induced by a single intravenous injection of NMU (nitrosomethylurea, 50 mg/kg) in female Sprague-Dawley rats (obtained from Tierzucht Schönwalde, age 50-55 days). Starting 10 days later, rats with at least one established tumor were treated for 4 weeks by: 1) solvent control, 2) ovariectomy at treatment start, 3) antiprogestin (I), 1.0 mg/kg/day, 4) antiprogestin (I), 0.5 mg/kg/day and 5) onapristone, 5 mg/kg/day. As a parameter for growth inhibition the change of tumor area (in % of initial tumor size) determined by weekly caliper measurements was used. For statistical analysis of intergroup differences of mean values the Kruskal-Wallis-test was used.

Results

Figure 4:
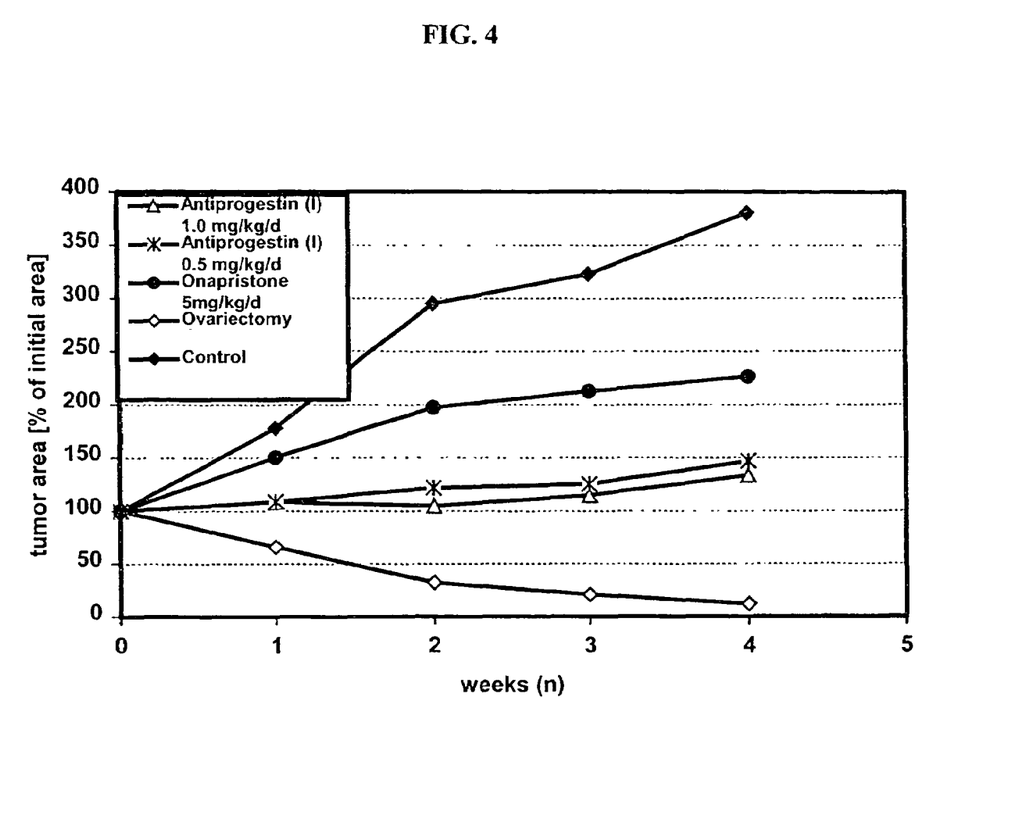
FIG. 4 shows the tumor growth inhibiting effect of 0.5 and 10.0 mg/kg doses of antiprogestin (I) in the NMU-induced mammary carcinoma of the rat, compared with a control, onapristone (5 mg/kg) and ovariectomy.

In intact control animals, progressive tumor growth was observed, whereas ovariectomy caused a complete tumor growth inhibition. Treatment with antiprogestin (I) at doses of 0.5 or 1.0 mg/kg resulted in a significant inhibition of tumor growth compared with the control (see FIG. 4). Onapristone (5 mg/kg) was distinctly less effective than antiprogestin (I) at the much lower dose of 0.5 mg/kg.

Conclusions:

In the MNU-induced mammary tumor model in the rat, antiprogestin (I) completely suppresses the tumor growth in intact animals. It was found that at a dose of 1.0 mg/kg and even at a dose of only 0.5 mg/kg antiprogestin (I) has a significant effect on tumor growth. Thus, antiprogestin (I) was superior to known antiprogestins like onapristone.

Example 5

T47D Human Xenograft (Therapy Experiment)

Materials and Methods

Female Fox Chase scid mice (M&B) were supplemented with estradiol pellets (Innovative Research of America). T47D breast cancer cells, obtained from cell culture and suspended in matrigel, were implanted s.c. in the inguinal region of the mice. Treatment was started when the tumors were approximately 25 mm$^2$ in size. Treatment was continued until progression of the tumors. Experimental groups were: 1) control (vehicle), 2) ovariectomy, 3) antiprogestin (I), 10 mg/kg s.c.Tumor area was determined by caliper measurements. The Kruskal Wallis test was used for statistical analysis of intergroup differences of mean values.

Results

Figure 5:
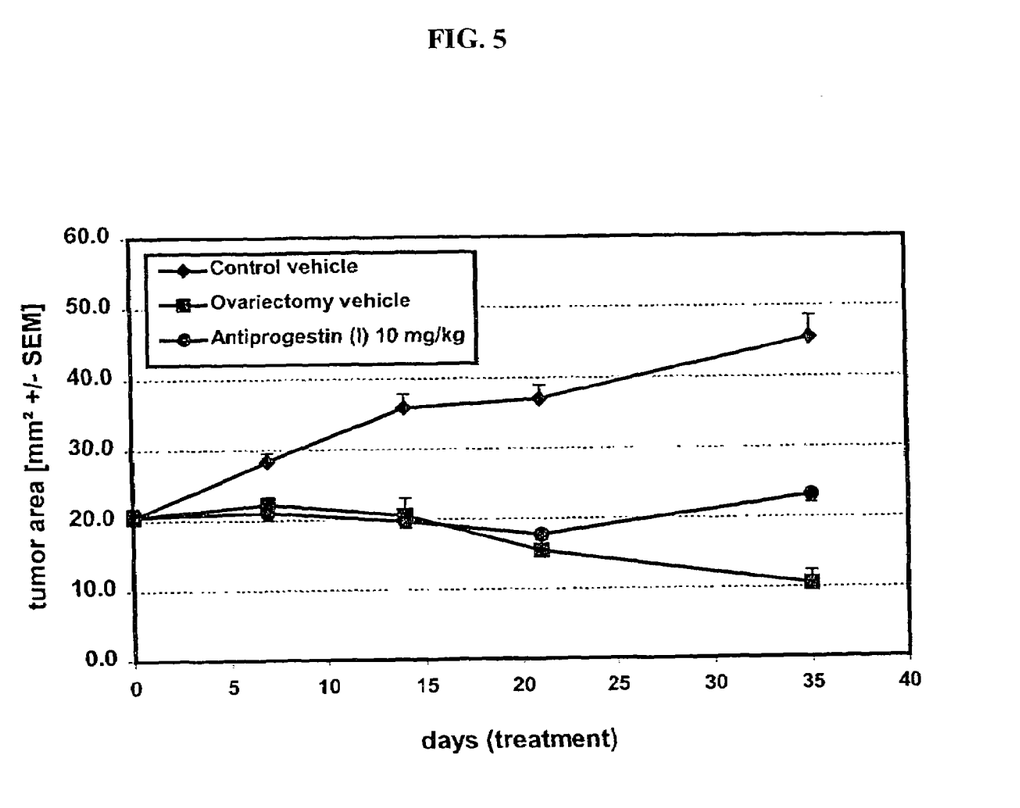
FIG. 5 shows the tumor growth inhibiting effect of antiprogestin (I) in a 10 mg/kg s.c. dose in the T47D human xenograft in scid mice, compared to a control as well as ovariectomy.

In the T47D breast cancer model, ovariectomy resulted in a considerable inhibition of tumor growth, compared with the rapid growth in the control. FIG. 5 shows that the s.c. application of 10 mg/kg antiprogestin (I) also caused an inhibition of tumor growth, almost comparable to the effect of conventional estrogen deprivation therapy (ovariectomy).

Conclusion

The effect of antiprogestin (I) in inhibiting the growth of the human T47D breast cancer xenografted in Fox Chase scid mice is comparable to the effect of standard estrogen deprivation therapy (ovariectomy) which is considered to be the maximum effective method of inhibiting growth of breast cancer in this model.

Example 6

MCF7 Human Xenograft (Therapy Experiment)

Materials and Methods

Female Fox Chase scid mice (M&B) were supplemented with estradiol pellets (Innovative Research of America). MCF7 breast cancer cells, obtained from cell culture and suspended in matrigel, were implanted s.c. in the inguinal region of the mice. Treatment was started when the tumors were approximately 25 mm$^2$ in size. Treatment was continued until progression of the tumors. Experimental groups were: 1) control (vehicle), 2) ovariectomy, 3) antiprogestin (I), 10 mg/kg s.c. Tumor area was determined by caliper measurements. The Kruskal Wallis test was used for statistical analysis of intergroup differences of mean values.

Results

Figure 6:
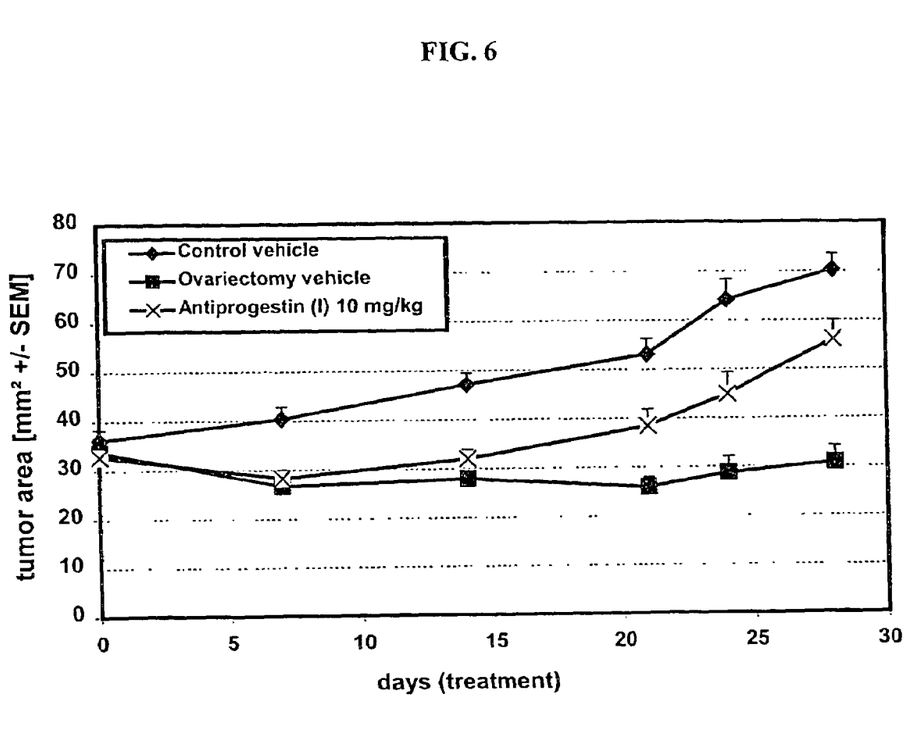
FIG. 6 shows the tumor growth inhibiting effect of antiprogestin (I) in a 10 mg/kg s.c. dose in the MCF7 human xenograft in scid mice, compared to a control as well as ovariectomy.

In the MCF7 breast cancer model, ovariectomy resulted in a considerable inhibition of tumor growth, compared with the rapid growth in the control. FIG. 6 shows that the s.c. application of 10 mg/kg antiprogestin (I) also caused an inhibition of tumor growth, almost comparable to the effect of conventional estrogen deprivation therapy (ovariectomy).

Conclusion

The effect of antiprogestin (I) in inhibiting the growth of the human MCF7 breast cancer xenografted in Fox Chase scid mice is comparable to the effect of standard estrogen deprivation therapy (ovariectomy) which is considered to be the maximum effective method of inhibiting growth of breast cancer in this model.

The invention claimed is:

1. A method for treating ovarian cancer, endometrial cancer, myeloma, anovulatory infertility, or meningoma in a mammal comprising administering to said mammal an effective amount of the antiprogestin 11β-(4-acetylphenyl)-17β-hydroxy-17α-(1,1,2,2,2-pentafluoroethyl)-estra-4,9-dien-3-one or a pharmaceutically acceptable salt thereof.

2. A method according to claim 1, wherein 11β-(4-acetylphenyl)-17β-hydroxy-17α-(1,1,2,2,2-pentafluoroethyl)-estra-4,9-dien-3-one is administered.

3. A method according to claim 1, wherein the antiprogestin 11β-(4-acetylphenyl)-17β-hydroxy- 17α-(1,1,2,2,2-pentafluoroethyl)-estra-4,9-dien-3-one or a pharmaceutically acceptable salt thereof is administered at a dose of >100 mg to 400 mg.

4. A method according to claim 1, wherein the antiprogestin 11β-(4-acetylphenyl)-17β-hydroxy-17α-(1,1,2,2,2-pentafluoroethyl)-estra-4,9-dien-3-one or a pharmaceutically acceptable salt thereof is administered orally.

5. A method according to claim 1, wherein the mammal is a human.

6. A method according to claim 1, wherein the disease is ovarian cancer.

7. A method according to claim 1, wherein the disease is endometrial cancer.

8. A method according to claim 1, wherein the disease is myeloma.

9. A method according to claim 1, wherein the disease is anovulatory infertility.

10. A method according to claim 1, wherein the disease is meningoma.

11. A method according to claim 6, wherein 11β-(4-acetylphenyl)-17β-hydroxy-17α-(1,1,2,2,2-pentafluoroethyl)-estra-4,9-dien-3-one is administered.

12. A method according to claim 7, wherein 11β-(4-acetylphenyl)-17β-hydroxy-17α-(1,1,2,2,2-pentafluoroethyl)-estra-4,9-dien-3-one is administered.

13. A method according to claim 8, wherein 11β-(4-acetylphenyl)-17β-hydroxy-17α-(1,1,2,2,2-pentafluoroethyl)-estra-4,9-dien-3-one is administered.

14. A method according to claim 9, wherein 11β-(4-acetylphenyl)-17β-hydroxy-17α-(1,1,2,2,2-pentafluoroethyl)-estra-4,9-dien-3-one is administered.

15. A method according to claim 10, wherein 11β-(4-acetylphenyl)-17β-hydroxy-17α-(1,1,2,2,2-pentafluoroethyl)-estra-4,9-dien-3-one is administered.

\* \* \* \* \*